United States Patent [19]

Cook

[11] 3,939,168

[45] Feb. 17, 1976

[54] 4-PIPERIDINE ACETAMIDES

[75] Inventor: Barry Cook, Manchester, England

[73] Assignee: Ciba-Geigy Corporation, Ardsley, N.Y.

[22] Filed: July 17, 1973

[21] Appl. No.: 380,040

[30] Foreign Application Priority Data

July 28, 1972 United Kingdom............... 35487/72

[52] U.S. Cl....260/293.77; 260/45.8 N; 260/45.8 NZ; 260/240 R; 260/240 K; 260/247.5 G; 260/270 R; 260/293.56; 260/293.62; 260/293.63; 260/293.64; 260/293.65; 260/293.66; 260/293.71; 260/293.73

[51] Int. Cl.$^2$........................................ C07D 211/32

[58] Field of Search..... 260/293.86, 293.66, 293.65, 260/293.63, 293.64, 293.73, 293.76, 293.85, 293.56, 293.62, 293.77

[56] References Cited

UNITED STATES PATENTS 3,498,992  3/1970  Kuhnis et al................... 260/293.86

OTHER PUBLICATIONS

C.A. 76:14299K (1972) Levkoeva et al.

Primary Examiner—Sherman D. Winters
Attorney, Agent, or Firm—Nestor W. Shust

[57] ABSTRACT

New piperidine derivatives and in particular esters and amides of substituted (piperidinyl-4) acetic acid are used as stabilisers for polymers, especially for polyolefines.

18 Claims, No Drawings

4-PIPERIDINE ACETAMIDES

The present invention provides a compound having the formula:

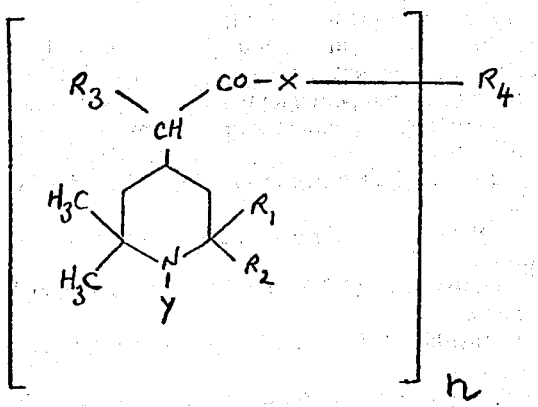

I wherein Y is a straight- or branched alkyl residue having from 1 to 12 carbon atoms, an alkenyl residue having from 3 to 12 carbon atoms, an aralkyl residue having from 7 to 12 carbon atoms or a group

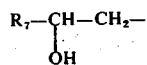

wherein $R_7$ is hydrogen, an alkyl residue having from 1 to 4 carbon atoms or a phenyl residue, $R_1$ or $R_2$ are the same or different and each is a straight- or branched alkyl residue having from 1 to 12 carbon atoms, or $R_1$ and $R_2$, together with the carbon atom to which they are attached form a cycloalkyl group having from 5 to 12 carbon atoms; $R_3$ is hydrogen, a straight- or branched alkyl residue having from 1 to 4 carbon atoms, an aralkyl residue having from 7 to 9 carbon atoms or a cycloalkyl group having from 5 to 6 carbon atoms, $R_4$ is hydrogen, a metal ion a hydrocarbyl residue having from 1 to 20 carbon atoms and being either unsubstituted or substituted by halogen or interrupted by one or more oxygen or sulphur atoms, or, when n is 1, $R_4$ can also have the structure:-

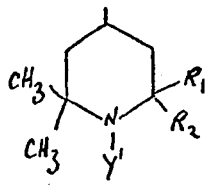

wherein $R_1$ and $R_2$ have their previous significance, Y' is hydrogen or has the same meaning as Y, X is -O-, -S- or >$NR_5$ wherein $R_5$ has the same significance as $R_3$ or when n is 1, in addition $R_4$ and $R_5$ together with nitrogen atom to which they are bound form a heterocyclic residue having from 4 to 10 carbon atoms and n is 1, 2, 3 or 4; as well as the salts of the amine function of the compounds of formula I.

When n is 1, $R_4$ can be for instance, hydrogen, a monovalent, straight- or branched aliphatic (either saturated or unsaturated) residue having from 1 to 20 carbon atoms, an alicyclic residue having from 5 to 20 carbon atoms, an aralkyl residue having from 7 to 12 carbon atoms, an aryl residue having from 6 to 15 carbon atoms, or $R_4$ and $R_5$ together with nitrogen atom to which they are bound form a heterocyclic residue having from 4 to 10 carbon atoms and optionally having one other heteroatom.

Examples of the group $R_4$ when n is 1 apart from hydrogen, are: methyl, ethyl, n-propyl, isopropyl, n-butyl, sec-butyl, t-butyl, n-pentyl, neopentyl, 2-ethylpropyl, 2-methylbutyl, n-hexyl, n-octyl, t-octyl, n-dodecyl, n-octadecyl, eicosyl, 2-methoxyethyl, 3-chloropropyl, 2-methyl thioethyl, allyl, α-methallyl, dec-9-enyl, heptadec-8-enyl, crotyl, cinnamyl, propargyl, 2,4-hexadienyl, benzyl, α-methylbenzyl, α,p-dimethylbenzyl, diphenylmethyl, 2-chlorobenzyl, cyclopentyl, cyclohexyl, cyclooctyl, 4-methylcyclohexyl, cyclododecyl, 4-chlorocyclohexyl, 9-fluorenyl, 1-adamantyl, phenyl, 4-methylphenyl, 4-t-octylphenyl, 2-chlorophenyl, 4-methoxyphenyl, α-naphthyl, 4-biphenyl, 2-fluorenyl and the group:

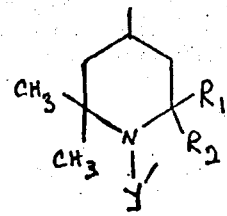

wherein $R_1$, $R_2$ and Y' have their previous significance. Examples of structures where $R_4$ and $R_5$ form a ring system, together with the nitrogen to which they are bound are 1-pyrrolidinyl, 1-piperidinyl and 1-morpholinyl.

When n is 2, $R_4$ may be a divalent, straight- or branched aliphatic residue (either saturated or unsaturated) having from 2 to 20 carbon atoms, a divalent alicyclic residue having from 5 to 20 carbon atoms, a divalent aralkyl residue having 8 to 20 carbon atoms, or a divalent aryl residue having 6 to 20 carbon atoms.

Examples of the group $R_4$ where n is 2 are 1,2-ethylene, 1,2-propylene, 1,4-n-butylene, 1,3-n-butylene 1,6-n-hexylene, 1,7-n-heptylene, 1,10-n-decylene, 1,12-n-dodecylene, 2,2-dimethyl-1,3-propylene, 1,2,3,-trimethyl-1,4-butylene, 3-thia-1,5-pentylene, 3-oxa-1,5-pentylene, 1,4-but-2-ynylene, 1,4-but-2-ynylene, 2,5-hex-3-enylene, 1,2-cyclohexylene, 1,3-cyclohexylene, 1,4-cyclohexylene, hexahydro-p-xylylene, p-xylylene, m-xylylene, 1,2-phenylene, 1,4-phenylene, 2,2'-biphenylene, 4,4'-biphenylene, 2,6-naphthylene and 2,7-fluoroenylene.

When n is 3, $R_4$ may be a trivalent straight- or branched chain aliphatic (either saturated or unsaturated) residue having 3 to 15 carbon atoms, a trivalent alicyclic residue having 5 to 15 carbon atoms, a trivalent aralkyl residue having from 9 to 15 carbon atoms, or a trivalent aryl residue having 6 to 15 carbon atoms.

Examples of the group $R_4$ when n is 3 are 1,2,3-tris substituted propane, 1,2,4-tri-substituted butane, 2,5-dimethyl-1,2,6-tri-substituted hexane, 1,1,1-trismethylenepropane, 1,2,3-tri-substituted cyclohexane, 1,3,5-tri-substituted cyclohexane, 1,3,5-trimethylenebenzene and 1,2,7-trisubstituted anthracene.

When n is 4, $R_4$ may be a straight- or branched chain tetravelent aliphatic residue (either saturated or unsaturated) having 4 to 12 carbon atoms or a tetravalent alicyclic residue having from 5 to 12 carbon atoms, such as tetramethylene methane and 1,1,4,4-tetramethylenecyclohexane.

When $R_4$ is an aliphatic, alicyclic, aryl or aralkyl residue, each of these residues may be unsubstituted or substituted by halogen or interrupted by one or more oxygen or sulphur atoms.

When $R_4$ is a metal ion, it is preferably a transition metal ion, more preferably an ion of a metal of Group VIII of the Periodic System of Elements, and especially as ion of nickel.

Examples of Y, in the compound of formula I, are methyl, ethyl, n-propyl, isopropyl, n-butyl, sec-butyl, n-hexyl, n-octyl, n-dodecyl, allyl, α-methallyl, 10-undecenyl, benzyl, α-methylbenzyl, p-methylbenzyl, α,p-dimethylbenzyl α-naphthylmethyl, 2-hydroxyethyl, 2-phenyl-2-hydroxyethyl and 2-hydroxypropyl residues.

Particularly preferred substituents Y are straight- or branched alkyl groups having from 1 to 4 carbon atoms and the most preferred value for Y is methyl.

Examples of the groups $R_1$ and $R_2$ are methyl, ethyl, n-propyl, isopropyl, n-butyl, sec-butyl, n-hexyl, n-dodecyl, or together with the carbon to which they are bound $R_1$ and $R_2$ can form a group such as

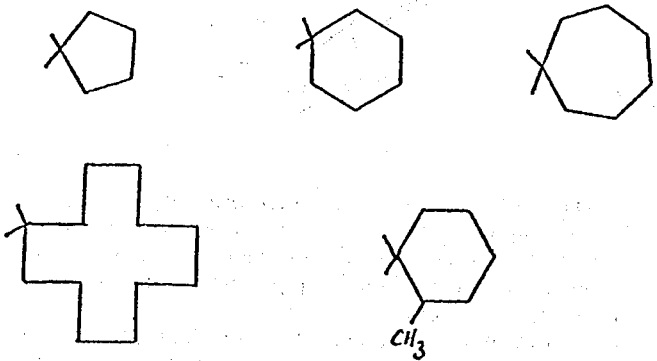

Particularly preferred substituents $R_1$ and $R_2$ are straight or branched alkyl groups having 1 to 4 carbon atoms and the most preferred value for each of $R_1$ and $R_2$ is methyl.

Examples of the groups $R_3$ and $R_5$ are hydrogen, methyl ethyl, n-propyl, isopropyl, n-butyl, sec-butyl, benzyl, α-methylbenzyl, α,p-dimethylbenzyl, cyclohexyl, cyclopentyl. Particularly preferred substituents $R_3$ and $R_5$ are hydrogen and an alkyl residue having from 1 to 4 carbon atoms and the most preferred substituent $R_3$ and $R_5$ is hydrogen.

Examples of salts of the compounds of formula I that can be used according to the invention include salts of an inorganic acid, such as phosphates, carbonates, sulphates, chlorides and the like, as well as organic acid salts such as acetates, stearates, maloates, citrates, tartrates, oxalates, benzoates and substituted carbamic acids.

Examples of the esters and amides of formula I envisaged are given in the following list:

(1,2,2,6,6-pentamethylpiperidinyl-4) acetic acid
ethyl (1,2,2,6,6-pentamethylpiperidimyl-4) acetate
n-butyl (1,2,2,6,6-pentamethylpiperidinyl-4) acetate
n-octyl (1,2,2,6,6-pentamethylpiperidinyl-4) acetate
2-octyl (1,2,2,6,6-pentamethylpiperidinyl-4) acetate
n-dodecyl (1,2,2,6,6-pentamethylpiperidinyl-4) acetate
n-octadecyl (1,2,2,6,6-pentamethylpiperidinyl-4) acetate
2'-methoxyethyl (1,2,2,6,6-pentamethylpiperidinyl-4) acetate
2'-methylthioethyl (1,2,2,6,6-pentamethylpiperidinyl-4) acetate
ethyl (1-ethyl-2,2,6,6-tetramethylpiperidinyl-4)acetate
n-ethyl (1-isobutyl-2,2-diethyl-6,6-dimethylpiperidinyl4)acetate
ethyl (1-methyl-2,2-diethyl-6,6-dimethylpiperidinyl-4) acetate
cyclohexyl (1,2,2,6,6-pentamethylpiperidinyl-4) acetate
4'-chlorocyclohexyl (1,2,2,6,6-pentamethylpiperidinyl-4) acetate
cyclododecyl (1,2,2,6,6-pentamethylpiperidinyl-4) acetate
benzyl (1,2,2,6,6-pentamethylpiperidinyl-4) acetate
4'-methoxybenzyl (1,2,2,6,6-pentamethylpiperidinyl-4) acetate
phenyl (1,2,2,6,6-pentamethylpiperidinyl-4) acetate
4-t-butylphenyl (1,2,2,6,6-pentamethylpiperidinyl-4) acetate
2'-chlorophenyl (1,2,2,6,6-pentamethylpiperidinyl-4) acetate
α-(n-butyl) ethyl (1,2,2,6,6-pentamethylpiperidinyl-4) acetate
allyl (1,2,2,6,6-pentamethylpiperidinyl-4) acetate
cinnamyl (1,2,2,6,6-pentamethylpiperidinyl-4) acetate
1',2'-ethylene di [(1,2,2,6,6-pentamethylpiperidinyl-4) acetate]
1,4-butylene di [(1,2,2,6,6-pentamethylpiperidinyl-4) acetate]
3'-oxa-,5'5'-pentylene di [(1,2,2,6,6-pentamethylpiperidinyl-4) acetate]
3'-thia-1',5'-pentylene di [(1,2,2,6,6-pentamethylpiperidinyl-4) acetate]

1',1',1'-tri [(1,2,2,6,6-pentamethylpiperidinyl-4) acetoxymethyl] propane tetrakis [(1,2,2,6,6-pentamethylpiperidinyl-4) acetoxymethyl] methane (2',2',6',6'-tetramethylpiperidinyl-4')[(1,2,2,6,6-pentamethylpiperidinyl-4) acetate]

ethyl (1,2,2,6,6-pentamethylpiperidinyl-4) thioacetate n-butyl (1,2,2,6,6-pentamethylpiperidinyl-4) thioacetate n-octyl (1,2,2,6,6-pentamethylpiperidinyl-4) thioacetate n-octadecyl (1,2,2,6,6-pentamethylpiperidinyl-4) thioacetate n-octyl(1(n-butyl)-2,2,6,6-tetramethylpiperidinyl-4) thioacetate 1',4'-butylene di (1,2,2,6,6-pentamethylpiperidinyl-4) thioacetate 1,10-decyclylene(1,2,2,6,6,-pentamethylpiperidinyl-4) thioacetate cyclohexyl (1,2,2,6,6-pentamethylpiperidinyl-4) thioacetate cyclohexyl (1-ethyl-2,2-di-isopropyl-6,6dimethylpiperidinyl-4) thioacetate allyl (1,2,2,6,6-pentamethylpiperidinyl-4) thioacetate cinnamyl (1,2,2,6,6-pentamethylpiperidinyl-4) thioacetate crotyl (1,2,2,6,6-pentamethylpiperidinyl-4) thioacetate benzyl (1,2,2,6,6-pentamethylpiperidinyl-4) thioacetate phenyl (1,2,2,6,6-pentamethylpiperidinyl-4) thioacetate (1,2,2,6,6-pentamethylpiperidinyl-4) acetamide N-n-butyl (1,2,2,6,6-pentamethylpiperidinyl-4) acetamide N-(n-hexyl)(1,2,2,6,6-pentamethylpiperidinyl-4) acetamide N-(n-octyl)(1,2,2,6,6-pentamethylpiperidinyl-4) acetamide N-(n-dodecyl)(1,2,2,6,6-pentamethylpiperidinyl-4) acetamide N-(n-octadecyl)1,2,2,6,6-pentamethylpiperidinyl-4) acetamide N-cyclohexyl (1,2,2,6,6-pentamethylpiperidinyl-4) acetamide N-cyclohexyl(1-ethyl-2,2,6,6-pentamethylpiperidinyl-4)acetamide N-benzyl (1,2,2,6,6-pentamethylpiperidinyl-4) acetamide N-phenyl (1,2,2,6,6-pentamethylpiperidinyl-4) acetamide N-(4'-chlorobutyl)(1,2,2,6,6-pentamethylpiperidinyl-4) acetamide N-(2'-methoxyphenyl)(1,2,2,6,6-pentamethylpiperidinyl-4) acetamide α-(n-butyl)-N-cyclohexyl (1,2,2,6,6-pentamethylpiperidinyl-4) acetamide N-allyl (1,2,2,6,6-pentamethylpiperidinyl-4) acetamide N-(2', 2', 6', 6'-tetramethylpiperidinyl-4)[(1,2,2,6,6-pentamethylpiperidinyl-4) acetamide]

N,N'-di[(1,2,2,6,6-pentamethylpiperidinyl-4) acetyl] ethane-1',2'-diamine

N,N'-di [(1,2,2,6,6-pentamethylpiperidinyl-4) acetyl] hexane-1',6'-diamine

1[((1',2',6',6'-pentamethylpiperidinyl-4') acetyl] morpholine

Oleyl(1,2,2,6,6-pentamethylpiperidinyl-4)acetate (α-isopropyl)-ethyl(1,2,6,6-pentamethylpiperidinyl-4)acetate (1,2,2,6,6-Pentamethylpiperidinyl-4)acetic acid hydrochloride N,N-Di(n-butyl)(1,2,2,6,6-pentamethylpiperidinyl-4)acetamide Ethyl(1-(n-dodecyl)-2,2,6,6-tetramethylpiperidinyl-4)acetate Ethyl(1-benzyl-2,2,6,6-tetramethylpiperidinyl-4)acetate Ethyl(1-allyl-2,2,6,6-tetramethylpiperidinyl-4)acetate Ethyl(1-propargyl-2,2,6,6-tetramethylpiperidinyl-4)acetate Ethyl[1-(2'-phenyl-2'-hydroxyethyl)2,2,6,6-tetramethylpiperidinyl-4]acetate Ethyl[1-(2'-hydroxyethyl)(2,2,6,6-tetramethylpiperidinyl-4] acetate Bis[(1,2,2,6,6-pentamethylpiperidinyl-4)acetato]-Nickel"

3,5,5-Trimethyl-1-[-(1',2',2',6',6'-tetramethylpiperidinyl-4')acetamido]-3[(1'',2'',2'',6'',-pentamethylpiperidinyl-4'') acetamido methyl]ctclohexane 1,12-dodecylene-di[(1',2',6',6'-pentamethylpiperidinyl-4')-acetate].

The present invention also provides a first preferred process in which a compound of formula I is produced comprising reacting a compound having the formula:

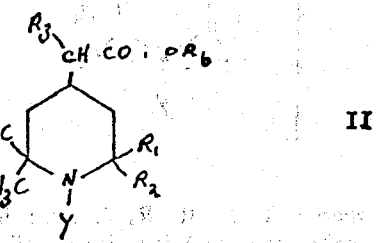

II wherein $R_1$, $R_2$, $R_3$ and Y have their previous significance and $R_6$ is hydrogen or an alkyl group having from 1 to 4 carbon atoms, with a compound having the formula:

$$R_4(XH)_n \qquad \qquad III$$

wherein $R_4$, X and n have their previous significance.

The reaction may be conveniently effected with or without the use of a catalyst and a solvent. If a catalyst is used however, it may be a lithium amide, an alkali metal alkoxide, p-toluene sulphonic acid, calcium hydroxide, tetra-n-butyl titanate or di-butyl tin oxide. If a solvent is used, the solvent is one which is inert to the reactants and the reaction product. Suitable solvents include benzene, xylene, cyclohexane and dioxan.

The reaction is preferably carried out at an elevated temperature, for instance at a temperature within the range of from 100° to 200°C. Advantageously, the alcohol $R_6OH$, which is produced during the reaction, is allowed to distil out of the reactor as it is formed.

If desired, the crude reaction product may be purified, for instance by solvent extraction and by subsequent recrystallisation from a suitable solvent, or by re-distillation.

The starting-material of formula II may be produced for example by hydrogenation of a compound having the formula:-

IV
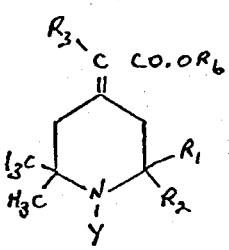

wherein $R_1$, $R_2$, $R_3$, $R_6$ and Y have their previous significance.

All starting-materials of formula II may be obtained by this route except those in which Y is alkenyl or aralkyl. In the case in which Y is alkenyl or aralkyl, the compound of formula II is obtained from the corresponding compound of formula IV in which Y is H, by hydrogenating this compound and then reacting the hydrogenated compound with the appropriate alkenyl or aralkyl halide.

In a second process, a compound of formula I is produced by hydrogenating a compound having the formula:-

V
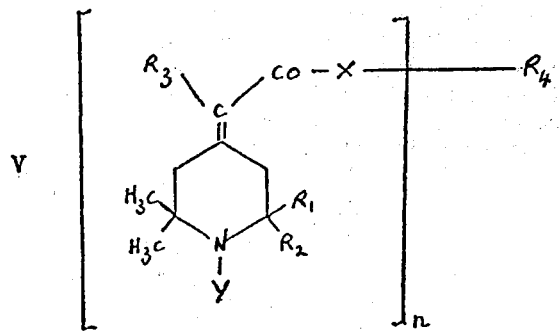

wherein $R_1$, $R_2$, $R_3$, $R_4$, X and n have their previous significance and Y is hydrogen, alkyl or aralkyl.

The hydrogenation of compounds IV and V may be conveniently effected using molecular hydrogen or using chemical means such as lithium aluminium hydride. If molecular hydrogen is used, the hydrogenation may be conducted in known manner using a hydrogenation catalyst such as palladium, platinum, rhodium or nickel, preferably supported on a carrier such as silica, calcium carbonate or carbon. Advantageously the reaction is conducted at elevated temperature and pressure, and in a suitable solvent such as ethanol or cyclohexane.

In a third, less preferred embodiment, a compound of formula I is produced by reacting a compound having the formula.

VI
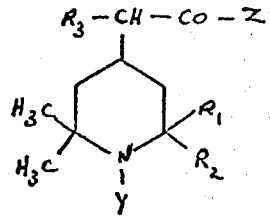

wherein $R_1$, $R_2$, $R_3$ and Y have their previous significance and Z is halogen, with a compound having the formula III as hereinbefore defined.

The reaction is conveniently effected in a solvent inert to the reactants and the reaction products. Suitable solvents include benzene, toluene, cyclohexane and dioxan. Advantageously the reaction is effected at an elevated temperature, preferably at the reflux temperature of the reaction mixture.

The starting-material of formula VI may be produced from the compound of formula II by method well-known per se.

In all processes of the present invention, instead of using starting-materials containing the group >N-Y, the corresponding >N-H compound may be used as starting-material, the group Y being introduced into the molecule during a subsequent reaction stage. Clearly, however, if the Y substituent to be introduced in this way is alkenyl or aralkyl, the introduction of this group must be made after any hydrogenation stage.

Alkyl, aralkyl or alkenyl groups may be introduced at the nitrogen atom of the piperidine ring by reacting the >N-H compound with the corresponding alkyl, aralkyl or alkenyl halide or by a Leuckart or Wallach reaction using the appropriate aldehyde or ketone. 2-Hydroxyalkyl or 2-hydroxyaralkyl substituents may be introduced by reacting the >N-H compound with the appropriate epoxide.

Salts of the compounds of formula I may be prepared by the reaction of the appropriate acid with a solution of a compound of formula I in an inert solvent.

Metal salts of formula I may be prepared by the reaction of a compound having the formula:-

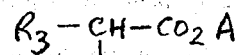
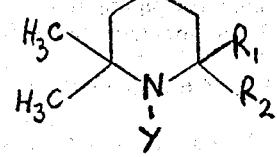

VII where $R_1$, $R_2$, $R_3$ and Y have their previous significance and A is an alkali metal ion, preferably sodium, with a compound of formula:

$$M(Z)_n \qquad \text{VIII}$$

where M is a metal ion, preferably a transition metal ion, especially nickel, Z is halogen, and n is 1,2,3, or 4.

The reaction is conveniently carried out in a solvent for instance, ethyl alcohol or water.

The present invention further provides a composition comprising an organic material and, as stabiliser, a minor proportion of a compound of formula I as hereinbefore defined.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabiliser of the invention provide effective light and/or heat stabilisation especially for low- and high-density polethylene and polypropylene and polystyrene as well as polymers of butene-1, pentene-1, 3-methylbutene-1, hexene-1, 4-methylpentene-1, 4-methylhexene-1 and 4,4-dimethylpentene-1, and also co- and ter-polymers of olefines, particularly of ethylene or propylene.

Other organic materials susceptible to degradation by the effects of light and the properties of which are improved by the incorporation therein of a compound of formula I include natural and synthetic polymeric materials, for instance natural and synthetic rubbers, the latter including, for example, homo-, co- and terpolymers or acrylonitrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamides; urea-formaldehyde and melamine -formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol ethanol or acetone to powdered polymer and the whole mixed intimately in a mixer; and the solvent subsequently removed. As a further alternative the compound of formula I may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass-fibres, kaolin and talc.

The present invention therefore includes binary, tertiary and multi-component compositions containing, as stabiliser, a compound of formula I together with one or more functional additives for polymers.

Examples of suitable antioxidants are those of the hindered phenol type such as those selected from the following groups:

I Phenolic compounds having the general formula $$Q-(CH_2)_w-A_1$$

wherein
Q is

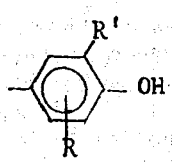

$A_1$ is $-CR(COOR'')_2$

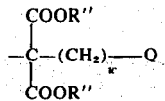

R is hydrogen or lower alkyl
R' is lower alkyl
R'' is alkyl group having from 6 – 24 carbon atoms
w is an integer from 0 to 4.

Illustrative examples of the compounds shown above are:
di-n-octadecyl-α-(3,5-di-t-butyl-4-hydroxy-benzyl) malonate
di-n-octadecyl-α-(3-t-butyl-4-hydroxy-5-methylbenzyl)malonate  di-n-octadecyl-α,α'bis-(3-t-butyl-4-hydroxy-5-methyl-benzyl)malonate 2 Phenolic compounds having the general formula $$Q-R'''$$

Illustrative examples of the compounds shown above are:
2,6-di-t-butyl-p-cresol
2-methyl-4,6-di-t-butylphenol and the like
2,6-di-Octadecyl-p-cresol (3) Phenolic compounds having the formula $$Q-C_wH_{2w}-Q$$

Illustrative examples of the compounds shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)-4-methylphenol
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol)  and the like.

(4) Phenolic compounds having the formula:

$$R'''-O-Q$$

Illustrative examples of such compounds are:
2,5-di-t-butylhydroquinone
2,6-di-t-butylhydroquinone
2,5-di-t-butyl-4-hydroxyanisole (5) Phenolic compounds having the formula:

$$Q-S-Q$$

Illustrative examples of such compounds are:
4,4'-thiobis-(2-t-butyl-5-methylphenol)
4,4'-thiobis-(2-t-butyl-6-methylphenol)
2,2'-thiobis-(6-t-butyl-4-methylphenol)
4,4'-thiobis-(2-methyl-5-t-butylphenol)

(6) Phenolic compounds having the formula $$Q-(CH_2)_w-S-(CH_2)_w-\overset{O}{\overset{\|}{C}}-OR''$$

Illustrative examples of such compounds are:
octadecyl-(3,5-dimethyl-4-hydroxybenzylthio)-acetate dodecyl-(3,5-di-t-butyl-4-hydroxybenzylthio)-propionate (7) Phenolic compounds having the formula

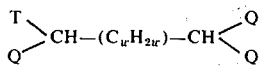

wherein T is hydrogen R or Q as defined above.
Illustrative examples of such compounds are:
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane (8) Phenolic compounds having the formula:

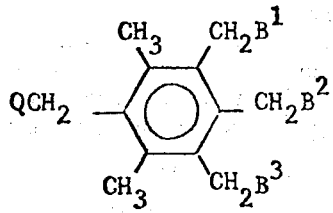

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl.
Illustrative examples of such compounds are:
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene (9) Phenolic compounds having the formula

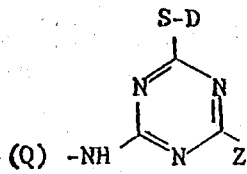

wherein Z is NHQ, -S-D- or -O-Q
D is alkyl group having from 6 – 12 carbon atoms or -($C_uH_{2u}$)-S-R''
Illustrative examples of such compounds are:
2,4bis-(n-octylthio)-6-(3,5-di-t-butyl-4-hydroxyaniline)-1,3,5-triazine
6-(4-hydroxy-3-methyl-5-t-butylanilino)-2,4-bis-(n-octylthio)-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine
6-(4-hydroxy-3,5-di-t-butylanilino)-4-(4-hydroxy-3,5-di-t-butylphenoxy)-2-n-octylthio)1,3,5-triazine
2,4-bis(4-hydroxy-3,5-di-t-butylanilino)-6-(n-octylthio)-1,3,5-triazine

(10) Phenolic compounds having the formula:

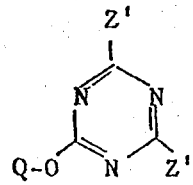

wherein Z' is -O-Q, -S-D or -S-($C_uH_{2u}$)-SD.
Illustrative examples of such compounds are:
2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

(11) Phenolic compounds having the formula

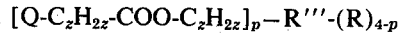

wherein p is an integer from 2 to 4 and R''' is a tetravalent radical selected from aliphatic hydrocarbons having from 1 to 30 carbon atoms, aliphatic mono- and dithioethers having from 1 to 30 carbon atoms, aliphatic mono- and diethers having from 1 to 30 carbon atoms and z is an integer from 0 to 6.
Illustrative examples of such compounds are Sub-class I n-Octadecyl-3-(3,5-di-t-butyl-4-hydroxyphenyl)-propionate
n-Octadecyl-2-(3,5-di-t-butyl-4-hydroxyphenyl)-acetate
n-Octadecyl-3,5-di-t-butyl-4-hydroxybenzoate
n-Hexyl-3,5-di-t-butyl-4-hydroxyphenylbenzoate
n-Dodecyl-3,5-di-t-butyl-4-hydroxyphenylbenzoate
Neo-dodecyl-3-(3,5-di-t-butyl-4-hydroxyphenyl)-propionate
Dodecyl-$\beta$-(3,5-di-t-butyl-4-hydroxyphenyl)-propionate
Ethyl-$\alpha$-(4-hydroxy-3,5-di-t-butylphenyl)-isobutyrate
Octadecyl-$\alpha$-(4-hydroxy-3,5-di-t-butylphenyl)-isobutyrate Octadecyl-α-(4-hydroxy-3,5-di-t-butylphenyl)-propionate Sub-class II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydoxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl) acetate
Diethyl glycol bis-[3,5-di-t-butyl-4-hydroxyphenyl) propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate Sub-class III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate]

(12) Phenolic compounds having the formula

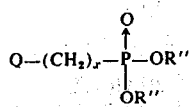

here $x$ is an integer of 1 or 2.
Illustrative examples of such compounds are

Di-n-octadecyl 3,5-di-t-butyl-4-hydroxybenzyl-phosphonate
Di-n-octadecyl 3-t-butyl-4-hydroxy-5-methylbenzylphosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexydecyl 3,5-di-t-butyl-4-hydroxybenzylphosphonate
Di-n-docosyl-3,5-di-t-butyl-4-hydroxybenzylphosphonate
Di-n-octadecyl 3,5-di-t-butyl-4-hydroxybenzylphosphonate.

(13) Phenolic compounds having the formula

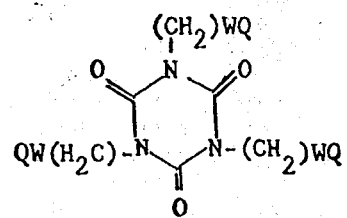

wherein W and Q are defined above.
Illustrative examples of such compounds are:
tris-(3,5-di-t-butyl-4-hydroxybenzyl)isocyanurate
tris-(3-t-butyl-4-hydroxy-5-methylbenzyl)isocyanurate.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:-
phenyl-1-naphthylamine
phenyl-2-naphthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include
(a) 2-(2'-hydroxyphenyl)benzotriazoles, for instance 5'-methyl; 3',5'-di-t-butyl; 5'-t-butyl; 5-chloro-3', 5'-di-t-butyl; 5-chloro-3'-t-butyl-5'-methyl; 3'-sec. butyl-5'-tert.butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbamethoxyethyl; 5-chloro-3',5'-di-t-amyl derivatives.

(b) 2,4-bis-(2'-hydroxyphenyl)-6-alkyl-S-triazines, for instance the 6-ethyl or 6-undecyl derivatives.

(c) 2-hydroxybenzophenones, for instance the 4-hydroxy, 4-methoxy, 4-octoxy-, 4-decyloxy-, 4-dodecyloxy-, 4,2',4'-trihydroxy or 2'-hydroxy-4,4'-dimethoxy derivatives.

(d) 1,3-Bis(2'-hydroxybenzoyl)-benzenes for instance,
1,3-bis-(2'-hydroxy-4'-hexyloxybenzoyl)benzene
1,3-bis-(2'-hydroxy-4'-octoxybenzoyl)benzene
1,3-bis-(2'-hydroxy-4'-dodecyloxybenzoyl)benzene (e) Aryl esters from optionally substituted benzoic acids such as phenylsalicylate, octylphenylsalicylate, dibenzoyl resorcinol, bis-(4-tert.butylbenzoyl) reesorcinol, benzoylresorcinol and 3,5-di-tert.butyl-4-hydroxy-benzoic acid-2,4-di-tert.butyl phenyl ester and -octadecyl ester and -2-methyl-4,6-di-tert.butyl phenyl ester.

(f) Acrylates, for instance

α-Cyano-β, β-diphenylacrylic acid ethyl- or iso-octyl ester, α-carbomethoxy-cinnamic acid, methyl- or butyl ester and N-(β-carbomethoxyvinyl)-2-methyl indoline.

(g) Nickel compounds such as nickel complexes of 2,2′-thiobis-(4-tert.octylphenol), for instance the 1:1 and 1:2 complexes, optionally having other ligands such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert.butylbenzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and (h) Oxalic acid diamides, for instance 4,4′-dioctyloxyoxanilide
2,2′-dioctyloxy-5,5′-di-tert.butyl-oxanilide
2,2′-di-dodecyloxy-5,5′-di-tert.butyl oxanilide
2-ethoxy-5-tertiarybutyl-2′-ethyl-oxanilide
2-ethoxy-2′-ethyl-oxanilide
mixtures of o- and p-methoxy and ethoxy-di-substituted
oxanilides and the compound of formula:

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert.butylphenyl)phosphite.

Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated organic materials.

In combination with an antioxidant suitable for use in inhibiting oxidative deterioration of polyolefines, for instance those of the hindered phenol type, the compounds of formula I provide extremely effective all round stabilising packages for polyolefines.

Some Examples will now be given. Parts and percentages shown therein are by weight unless otherwise stated.

EXAMPLE 1

15.9 Parts by weight of ethyl(2,2,6,6-tetramethylpiperidinyl-4)acetate, 9.8 parts by weight of 98% formic acid, and 6.5 parts by weight of formaldehyde were heated with stirring at 100°C for 15 hours. The solution was then cooled and 50 parts by volume of water added followed by 10 parts by volume of 46% aqueous sodium hydroxide. The resulting suspension was extracted with 6 × 50 parts by volume of ether, the combined ether extracts were then dried over magnesium sulphate and the ether removed by distillation to give crude ethyl(1,2,2,6,6-pentamethylpiperidinyl-4)acetate, which upon distillation gave 6.5 parts by weight (39% of theory yield) or pure material boiling at 150°–2°C/12 mmHg and having the following elemental analysis by weight:

|  | C | H | N |
|---|---|---|---|
| Found | 69.42 | 11.24 | 5.71% |
| Calculated for $C_{14}H_{27}NO_2$ | 69.67 | 11.27 | 5.80% |

EXAMPLE 2

7.5 parts by weight of ethyl(1,2,2,6,6-pentamethylpiperidinyl-4)acetate, 8.4 parts by weight of n-octadecanol and 1 part by weight of lithium amide were heated with stirring at 160°C/760 mmHg for 30 minutes, then at 160°C/12 mmHg for 10 minutes, the resulting mass was cooled and poured into 100 parts by volume of water, which was then extracted with 4 × 50 parts by volume of ether. The combined ether extracts were dried over magnesium sulphate and the crude product was dissolved in 20 parts by volume of petroleum ether (boiling range 60°–80°C) and the insoluble material removed by filtration. A white solid was obtained on evaporation of the petroleum ether solution at a bath temperature of 100°C and 12 mmHg. On drying this material at 100°C/0.1 mmHg for 8 hours, was obtained 6.8 parts by weight(47% of theory yield) of pure n-octadecyl(1,2,2,6,6-pentamethylpiperidinyl-4)-acetate, melting at 35°–6°C and having the following elemental analysis by weight:

|  | C | H | N |
|---|---|---|---|
| Found | 77.48 | 12.73 | 2.77% |
| Calculated for $C_{30}H_{59}NO_2$ | 77.36 | 12.77 | 3.01% |

EXAMPLE 3

8.5 Parts by weight of ethyl(1,2,2,6,6-pentamethylpiperidinyl-4)acetate, 3.5 parts by weight of cyclohexylamine, and 0.35 parts by weight of sodium methoxide were heated with stirring at 100°C/760 mmHg for 30 minutes, then at 160°C/760 mmHg for 20 minutes, and finally at 160°C/12 mmHg for 5 minutes. The resulting mass was cooled and triturated with water (100 parts by volume), the resulting white solid was collected by filtration, dried at 60°C and recrystallised from 50 parts by volume of petroleum ether (boiling range 60°–80°C) to give 5.5 parts by weight (54% of theory yield) of pure N-cyclohexyl(1,2,2,6,6-pentamethylpiperidinyl-4)acetamide, melting at 142°–3°C and having the following elemental analysis by weight:

|  | C | H | N |
|---|---|---|---|
| Found | 73.50 | 11.64 | 9.12% |
| Calculated for $C_{18}H_{34}N_2O$ | 73.42 | 11.64 | 9.51% |

EXAMPLE 4

12 parts by weight of ethyl(1,2,2,6,6-pentamethylpiperidinyl-4)acetate, 7.8 parts by weight of n-octanol, and 0.5 parts by weight of sodium methoxide were heated at 160°C. for 45 minutes, during which ethanol was removed by distillation from the flask. The resulting oil was poured into water and extracted with ether (4 × 50 parts by volume). The combined ether extracts, after drying over magnesium sulphate, were evaporated off under reduced pressure and the residual oil purified by distillation to give 7.8 parts by weight (48% of theory yield of n-octyl(1,2,2,6,6-penta-methylpiperidinyl-4)acetate b. 138°–40°C./0.4 mm. having the following elemental analysis by weight:

Found: C, 74.04; H, 11.92; N, 4.34% Required for $C_{20}H_{39}NO_2$: C, 73.79; H, 12.08; N, 4.30%

EXAMPLE 5

2.7 parts by weight of butane-1,4-diol, 13.6 parts by weight of ethyl(1,2,2,6,6-pentamethylpiperidinyl-4)acetate, and 0.5 parts by weight of lithium amide were heated at 160° for 1 hour. The resulting oil was worked up as in Example 4 to give 5.8 parts by weight (50% of theory yield) of 1,4-Butylene-di[(1′,2′,2′,6′,6′-pentamethylpiperidinyl-4′)acetate], b.p. 240°C/0.2 mm., having the following elemental analysis by weight:

Found: C, 69.75; H, 10.91; N, 5.89% Required for $C_{28}H_{52}N_2O_4$: C, 69.96; H, 10.90; N, 5.83%.

EXAMPLE 6

19.3 parts by weight of ethyl(1,2,2,6,6-pentamethylpiperidinyl-4)acetate, 1.7 parts by weight of pentacrythritol, and 1 part by weight of lithium amide were reacted as in Example 5 to give 7.4 parts by weight (80% of theory yield) of tetrakis [(1,2,2,6,6-pentamethylpiperidinyl-4)acetoxymethyl]methane having the following elemental analysis by weight:

Found: C, 69.24; H, 10.21; N, 5.88% Required for $C_{53}H_{96}N_4O_8$: C, 69.4; H, 10.47; N, 6.11%.

EXAMPLE 7

14.5 parts by weight of ethyl(1,2,2,6,6-pentamethylpiperidinyl-4)acetate, 10 parts by weight of cyclohexanol and 0.5 parts by weight of lithium amide were reacted as in Example 2 and worked up to give 9.3 parts by weight (31% of theory yield) of cyclohexyl(1,2,2,6,6-pentamethylpiperidinyl-4)acetate boiling at 155°C./0.7 mm. and having the following elemental analysis by weight:

Found: C, 73.45; H, 11.09; N, 4.60% Required for: C, 73.17; H, 11.26; N, 4.75% $C_{18}H_{33}NO_2$.

EXAMPLE 8

3.1 parts by weight of 1,2-ethane diol, 24.1 parts by weight of ethyl (1,2,2,6,6-pentamethylpiperidinyl-4)acetate, and 1.0 part by weight of lithium amide were reacted as in Example 5, to give 7.5 parts by weight (33% of theory yield) of 1,2-ethylene di[(1′,2′,2′,6′,6′-pentamethylpiperidinyl-4′) acetate], boiling at 221°C./0.4 mm.Hg. and having the following elemental analysis by weight:

Found: C, 69.13; H, 10.46; N, 6.08% Required for $C_{26}H_{48}N_2O_4$: C, 68.99; H, 10.69; N, 6.19%.

EXAMPLE 9

30 parts by weight of ethyl (1,2,2,6,6-pentamethylpiperidinyl-4) acetate, 3.0 parts by weight of 1,2-diamino ethane and 5.4 parts by weight of sodium methoxide were heated with stirring initially at 100°C.; the temperature of the reaction mixture was raised to 160°C. over 15 minutes at which temperature ethyl alcohol was distilled from the reaction flask. Reaction conditions were maintained at 160°C/760 mm. for 1 hour then at 100°C/12 mm. for 10 minutes. The residual mass was cooled, triturated with water and filtered. Recrystallisation from 300 parts by volume of ethyl acetate gave 27.3 parts by weight (77% of theory yield) of pure N,N′-di [(1′,2′,2′,6′,6′-pentamethylpiperidinyl-4-) acetyl] ethane-1,2-diamine, melting at 210°C. and having the following elemental analysis by weight:

Found: C, 69.22; H, 11.19; N, 12.38% Reqiured for $C_{26}H_{50}N_4O_2$: C, 69.29; H, 11.18; N, 12.43%.

EXAMPLE 10

14.5 Parts by weight of ethyl(1,2,2,6,6-pentamethylpiperidinyl-4)acetate, 11.2 parts by weight of n-dodecylamine, and 1.62 parts by weight of sodium methoxide were heated together, with stirring at 100°C for 20 minutes, the temperature was then raised to 160°C for a further 1 hour. Ethyl alcohol was allowed to distil from the reaction. The mixture was then cooled and poured into water. The product was extracted with ether and isolated as in Example 1 and purified by distillation to give 10.5 parts by weight (46% theory yield), of N-dodecyl (1,2,2,6,6-pentamethylpiperidinyl-4)acetamide boiling at 228°–30°C/0.7mm. and having the following elemental analysis by weight:

|  | C | H | N |
|---|---|---|---|
| Found: | 76.08 | 12.44 | 7.63% |
| Required for $C_{24}H_{48}N_2O$ | 75.73 | 12.71 | 7.36% |

EXAMPLE 11

A mixture of 12.1 parts by weight of ethyl (1,2,2,6,6-pentamethylpiperidinyl-4)acetate, 6.5 parts by weight of benzyl alcohol and 1 part by weight of lithium amide were treated as in Example 5 to give 1.9 parts by weight of benzyl(1,2,2,6,6-pentamethylpiperidinyl-4)acetate, boiling at 150°–2°C./0.5 mm and having the following elemental analysis by weight:

|  | C | H | N |
|---|---|---|---|
| Found | 75.50 | 9.91 | 4.75% |
| Required for $C_{19}H_{29}NO_2$ | 75.21 | 9.63 | 4.62% |

EXAMPLE 12

A mixture of 12.1 parts by weight of ethyl(1,2,2,6,6-pentamethylpiperidinyl-4)acetate, 10.1 parts by weight of n-hexylamine and 2.7 parts by weight of sodium methoxide were treated as in Example 10 to give 4.7 parts by weight of N-(n-hexyl)(1,2,2,6,6-pentamethylpiperidinyl-4)acetamide, boiling at 182°–4°C./0.8 mm, and having the following elemental analysis by weight:

|  | C | H | N |
|---|---|---|---|
| Found | 72.73 | 11.94 | 9.55% |
| Required for $C_{18}H_{36}N_2O$ | 72.92 | 12.24 | 9.45% |

EXAMPLE 13

A mixture of 18.5 parts by weight of ethyl(1,2,2,6,6-pentamethylpiperidinyl-4)acetate, 3.5 parts by weight of hexane-1,6-diamine, and 3.6 parts by weight of sodium methoxide were treated as in Example 10 to give a white solid, which by recrystallisation from cyclohexane gave 12.3 parts by weight (81% of theory yield) of pure N,N'-di[(1',2',2',6',6'-pentamethylpiperidinyl-4')acetyl]hexane-1,6-diamine, melting at 150°–2°C. and having the following elemental analysis by weight:

|  | C | H | N |
|---|---|---|---|
| Found | 70.90 | 11.30 | 10.97% |
| Required for $C_{30}H_{58}N_4O_2$ | 71.10 | 11.54 | 11.05% | pressure was applied. The pressure was then increased up to a maximum of 12 tons and this pressure held for 6 minutes, the temperature of the press being 260°C. The pressure was released and the material (0.3 mm thick) was cooled and running water.

This material was cut into from 3 to 5 pieces of 35 × 35 mm section and re-charged to the press. The press was closed and no pressure was applied for 2 minutes. Over another 2 minutes the pressure was increased to 8 tons, the press temperature being 260°C. This pressure was maintained for 2 minutes and then the pressure released. The polypropylene foil of 0.1 mm thickness was removed and tempered immediately in a circulating air oven maintained at 150°C over a period of 60 minutes.

A section measuring 44 × 100 mm was separated from the 0.1 mm tempered polypropylene foil and exposed to light irradiation in a fademeter device consisting of a circular bank of 28 alternating sunlight and blacklight lamps. The sunlight lamps were 2 feet long, 20-watt fluorescent lamps characterised by a peak emission of 3100 Angstrom units; the blacklight lamps were 2 feet long, 20 watt ultraviolet lamps characterised by a peak emission of 3500 Angstrom units. The sample was rotated concentrically about the bank of lamps so that the radiation therefrom was uniformly distributed over the section under test.

The exposed sample was examined periodically, when portions of it were removed for tensile testing and the time (T) was determined after which the elongation of the sample had decreased to 50% of the initial elongation.

The results obtained, including the use of other compounds of the invention as stabiliser are set out in the following table.

| Example | Additive | FACTOR Time (T) for additive Time (T) for control |
|---|---|---|
| — | None (control) | 1 |
| 14 | Ethyl(1,2,2,6,6-pentamethylpiperidinyl-4)acetate | 7.6 |
| 15 | n-Octadecyl (1,2,2,6,6-pentamethylpiperidinyl-4)acetate | 5.1 |
| 16 | N-Cyclohexyl (1,2,2,6,6-pentamethyl-4)acetamide | 4.7 |
| 17 | Ethane-1,2-di[(1',2',6',6'-pentamethylpiperidinyl-4') acetate] | 7.1 |
| 18 | Benzyl(1,2,2,6,6-pentamethylpiperidinyl-4')acetate | 6.3 |
| 19 | Di[(1',2',2',6',6-pentamethylpiperidinyl-4')acetyl]ethane-1,2-diamine | 6.3 |
| 20 | Di[(1',2',2',6',6'-pentamethylpiperidinyl-4')acetyl]hexane-1,6-diamine | 5.7 |
| 21 | N-(n-Dodecyl)(1,2,2,6,6-pentamethylpiperidinyl-4)acetamide | 5.4 |

EXAMPLES 14 TO 21

38 parts of polypropylene were homogenised with 0.076 parts of n-octadecyl-β-(4'-hydroxy-3',5'-t-butylphenyl) propionate in a kneading machine over a period of 3 minutes at 200°C. 0.19 parts of the product of Example 1 was then added and homogenisation continued for another 7 minutes.

The homogenised mixture was removed from the kneader and pressed to a thickness of from 2 to 3 mm. in a press.

9 parts of the polypropylene mixture were then charged into a second press in which the press-plates were protected by aluminium foil having a thickness of 0.1 mm. The press was closed and, for 2 minutes, no

EXAMPLE 22

A solution of 4.5 parts by weight of ethyl(2,2,6,6-tetramethylpiperidinyl-4)acetate and 30 parts by volume of styrene oxide in 30 parts by volume of n-hexanol was heated at reflux for 24 hours. The resulting solution was distilled to give ethyl[1-(2'-hydroxy-2'-phenylethyl) 2,2,6,6-tetramethylpiperidinyl-4]acetate, boiling at 190°C/0.9 mm mercury, and having the following elemental analysis by weight:

|  | C | H | N |
|---|---|---|---|
| Found | 72.52 | 9.27 | 3.90% |
| Required for $C_{21}H_{33}NO_3$ | 72.58 | 9.57 | 4.03% |

EXAMPLE 23

A solution of 22.7 parts by weight of ethyl(2,2,6,6-tetramethylpiperidinyl-4)acetate and 8.55 parts by weight of benzyl bromide in 100 parts by volume of dry toluene was heated at reflux for 42 hours.

The resulting suspension was cooled and the white crystals which formed were removed by filtration. The liquid was distilled to give 11.5 parts by weight (72% of theory yield) of ethyl(1-benzyl-2,2,6,6-tetramethylpiperidinyl-4 acetate, boiling at 142°–6°C./0.25 mm mercury and having the following elemental analysis by weight:

|  | C | H | N |
|---|---|---|---|
| Found | 75.74 | 10.12 | 4.44% |
| Required for $C_{20}H_{31}NO_2$ | 75.67 | 9.84 | 4.41% |

EXAMPLE 24

A solution of 22.7 parts by weight of ethyl(2,2,6,6-tetramethylpiperidinyl-4)acetate and 6.05 parts by weight of allylbromide in 100 parts by volume of toluene was treated as in Example 23 to give ethyl(1-allyl-2,2,6,6-tetramethylpiperidinyl-4)acetate boiling at 92°–6°C./0.3 mm mercury and having the following elemental analysis by weight:

|  | C | H | N |
|---|---|---|---|
| Found | 71.61 | 10.50 | 5.40% |
| Required for $C_{16}H_{29}NO_2$ | 71.83 | 10.93 | 5.24% |

EXAMPLE 25

22.7 Parts by weight of ethyl(2,2,6,6-tetramethylpiperidinyl-4)acetate and 12.45 parts by weight of n-dodecyl bromide were heated together at 100°C. for 80 hours. The suspension was cooled and diluted with 100 parts by volume of petroleum ether (boiling range 40°–60°C), the resulting solid was filtered and the liquid distilled to give ethyl[1-(n-dodecyl)-2,2,6,6-tetramethylpiperidinyl-4]acetate boiling at 178°–80°C./0.3 mm mercury and having the following elemental analysis by weight:

|  | C | H | N |
|---|---|---|---|
| Found | 76.15 | 12.66 | 3.58% |
| Required for $C_{25}H_{49}NO_2$ | 75.89 | 12.48 | 3.54% |

EXAMPLE 26

A solution of 22.7 parts by weight of ethyl(2,2,6,6-tetramethylpiperidinyl-4)acetate and 5.95 parts by weight of propargylbromide in 100 parts by volume of ethyl alcohol was heated at reflux for 20 hours.

The ethyl alcohol solvent was then distilled off under reduced pressure and the resulting solid was extracted with petroleum ether (boiling range 40°–60°C). The ether was stripped off under reduced pressure and the residual oil was distilled to give ethyl(1-propargyl-2,2,6,6-tetramethylpiperidinyl-4)acetate boiling at 97°–102°C./0.3 mm mercury and having the following elemental analysis by weight:

|  | C | H | N |
|---|---|---|---|
| Found | 72.28 | 10.02 | 5.34% |
| Required for $C_{16}H_{27}NO_2$ | 72.19 | 10.25 | 5.28% |

EXAMPLE 27

A solution of 30 parts by weight ethyl(1,2,2,6,6-pentamethylpiperidinyl-4)acetate in 200 parts by volume of 18% hydrochloric acid was heated at reflux for 4 hours. The volume of the solution was then reduced to 50 parts, by distillation under reduced pressure, and the solid so formed was collected by filtration, and washed with dry acetone. There were thus obtained 26 parts by weight (84% of theory yield) of (1,2,2,6,6-pentamethylpiperidinyl-4)acetic acid hydrochloride, decomp. <200°C., and having the following elemental analysis by weight:

|  | C | H | N | Cl |
|---|---|---|---|---|
| Found | 57.87 | 9.39 | 5.50 | 14.12% |
| Required for $C_{12}H_{24}ClNO_2$ | 57.70 | 9.62 | 5.61 | 14.19% |

EXAMPLE 28

2.5 Parts by weight of (1,2,2,6,6-pentamethylpiperidinyl-4)acetic acid hydrochloride and 50 parts by volume of thionyl chloride were heated together at reflux for 3 hours. The solution was evaporated to dryness by distillation under reduced pressure and the resulting solid dissolved in 60 parts by volume of dry 1,4-dioxan. 10 Parts by volume of di-n-butylamine were added and the solution heated to reflux for 4 hours. The solid precipitate (di-n-butylamine hydrochloride) was removed by filtration and the liquid remaining was distilled to give N,N-di(n-butyl) (1,2,2,6,6-pentamethylpiperidinyl-4)acetamide boiling at 170°–2°C./0.8 mm which was identified by p.m.r. spectra and had the following elemental analysis by weight:

|  | N |
|---|---|
| Found | 8.41% |
| Required for $C_{20}H_{40}N_2O$ | 8.63% |

EXAMPLE 29

A mixture of 12.5 parts by weight of ethyl(1,2,2,6,6-pentamethylpiperidinyl-4)acetate, 7.85 parts by weight of 2,2,6,6-tetramethylpiperidinyl-4-01 and 0.5 parts by weight of lithium amide was heated at 160°C. for 2 hours, during which time ethyl alcohol was removed by distillation.

The suspension was worked up as in Example 4 to give (2',2',6',6'-tetramethylpiperidinyl-4'-) (1,2,2,6,6-pentamethylpiperidinyl-4)acetate, boiling at 165°–9°C./0.8mm mercury and having the following elemental analysis by weight:

|        | C     | H     | N     |
|--------|-------|-------|-------|
| Found  | 71.80 | 11.70 | 8.02% |
| Required for $C_{21}H_{40}N_2O_2$ | 71.54 | 11.44 | 7.95% |

EXAMPLE 30

A solution of 10 parts by weight of ethyl(1,2,2,6,6-pentamethylpiperidinyl-4)acetate in 150 parts by volume of methyl alcohol saturated with ammonia was allowed to stand at room temperature for 4 weeks. The solution was evaporated to dryness and the residue recrystallised from ethyl acetate to give (1,2,2,6,6-pentamethylpiperidinyl-4)acetamide, melting at 121°–2°C. and having the following elemental analysis by weight:

|        | C     | H     | N      |
|--------|-------|-------|--------|
| Found  | 68.01 | 11.93 | 13.14% |
| Required for $C_{12}H_{24}N_2O$ | 67.88 | 11.39 | 13.19% |

EXAMPLE 31

A mixture of 12.1 parts by weight of ethyl(1,2,2,6,6-pentamethylpiperidinyl-4)acetate, 13.4 parts by weight of oleyl alcohol and 0.5 part by weight of lithium amide was treated as in Example 4 to give oleyl(1,2,2,6,6-pentamethylpiperidinyl-4)acetate boiling at 224°–8°C./0.4 mm and having the following elemental analysis by weight:

|        | C     | H     | N     |
|--------|-------|-------|-------|
| Found  | 77.99 | 12.22 | 3.13% |
| Required by $C_{30}H_{57}NO_2$ | 77.69 | 12.39 | 3.02% |

EXAMPLE 32

A solution of 2.5 parts by weight of (1,2,2,6,6-pentamethylpiperidinyl-4)acetic acid hydrochloride in 50 parts by volume of thionyl chloride was heated at reflux for 4 hours, the thionyl chloride was then removed by distillation under reduced pressure and the residual gum was dissolved in 50 parts by volume of dioxan. A solution of 10 parts by volume of aniline in 10 parts by volume of dioxan was then added and the resulting suspension heated at reflux for 18 hours.

The solid precipitate was removed by filtration and the dioxan and excess aniline were removed by distillation under reduced pressure. The residue was dissolved in 100 parts by volume of water and treated with 40% sodium hydroxide solution to pH 14, to give an oil which was extracted with 3 × 50 parts by volume of ether, the combined ether extracts were dried over magnesium sulphate and the ether removed by distillation. The resulting solid was recrystallised from cyclohexane to give N-phenyl-(1,2,2,6,6-pentamethylpiperidinyl-4)acetamide, melting at 146°C. and having the following elemental analysis by weight:

|        | C     | H    | N     |
|--------|-------|------|-------|
| Found  | 75.14 | 9.66 | 9.53% |
| Required for $C_{18}H_{28}N_2O$ | 75.96 | 9.78 | 9.71% |

EXAMPLE 33

A mixture of 19.3 parts by weight of ethyl(1,2,2,6,6-pentamethylpiperidinyl-4)acetate, 3.2 parts by weight of diethylene glycol and 0.5 parts by weight of lithium amide were treated as in Example 8 to give 3′-oxa-1′,5′-pentylenedi[(1,2,2,6,6-pentamethylpiperidinyl-4)acetate], boiling at 240°–2°C./0.4 mm, and having the following elemental analysis by weight:

|        | C     | H     | N     |
|--------|-------|-------|-------|
| Found  | 67.58 | 10.13 | 5.48% |
| Required for $C_{28}H_{52}N_2O_5$ | 67.70 | 10.50 | 5.64% |

EXAMPLE 34

A mixture of 12.1 parts by weight ethyl (1,2,2,6,6-pentamethylpiperidinyl-4)acetate, 4.5 parts by weight of 2-ethoxyethanol and 0.5 parts by weight of lithium amide was reacted as in Example 4 to give 2′-ethoxyethyl(1,2,2,6,6-pentamethylpiperidinyl-4)acetate boiling at 182°–4°C./12 mm and having the following elemental analysis by weight:

|        | N     |
|--------|-------|
| Found  | 5.16% |
| Required for $C_{16}H_{31}NO_3$ | 4.91% |

EXAMPLE 35

A mixture of 19.3 parts by weight of ethyl(1,2,2,6,6-pentamethylpiperidinyl-4)acetate, 6.1 parts by weight of dodecane-1,12-diol and 0.5 parts by weight of lithium amide was reacted as in Example 8 to give 1,12-dodecenyl-di[(1′,2′,2′,6′,6′-pentamethylpiperidinyl-4′) acetate], boiling at 260°–5°C./0.3 mm and having the following elemental analysis by weight:

|        | C     | H     | N     |
|--------|-------|-------|-------|
| Found  | 72.62 | 11.31 | 4.91% |
| Required for $C_{36}H_{68}N_2O_4$ | 72.92 | 11.56 | 4.72% |

EXAMPLE 36

A mixture of 14.5 parts by weight of ethyl(1,2,2,6,6-pentamethylpiperidinyl-4)acetate, 2.2 parts by weight of 2-butene-1,4-diol and 0.5 parts by weight of lithium amide was reacted as in Example 8 to give 2-butene-1,4-di[(1′,2′,2′,6′,6′-pentamethylpiperidinyl-4′)acetate], boiling at 220°C./0.3 mm and having the following elemental analysis

|        | C     | H     | N     |
|--------|-------|-------|-------|
| Found  | 70.47 | 10.24 | 5.77% |
| Required by $C_{28}H_{50}N_2O_4$ | 70.75 | 10.53 | 5.85% |

EXAMPLE 37

A solution of 2.4 parts by weight of nickel chloride hexahydrate in 40 parts by volume of ethyl alcohol was added to a stirred solution of 4.7 parts by weight of sodium [(1,2,2,6,6-pentamethylpiperidinyl-4)acetate](prepared by the hydrolysis of ethyl (1,2,2,6,6-pentamethylpiperidinyl-4)acetate in dilute sodium hydroxide) in 60 parts by volume of ethyl alcohol at reflux temperature. The resulting solution was heated at reflux for a further 4 hours then cooled and the insoluble material removed by filtration. Ethyl alcohol was removed by distillation under reduced pressure and the residual solid extracted with chloroform. A small amount of insoluble material was removed by filtration and the solution was then evaporated to dryness under reduced pressure to give a green solid nickel salt having the following elemental analysis by weight:

Carbon: 54.66%
Hydrogen: 8.95%
Nitrogen: 4.96%
Nickel: 8.1%

I claim:
1. A compound of the formula I

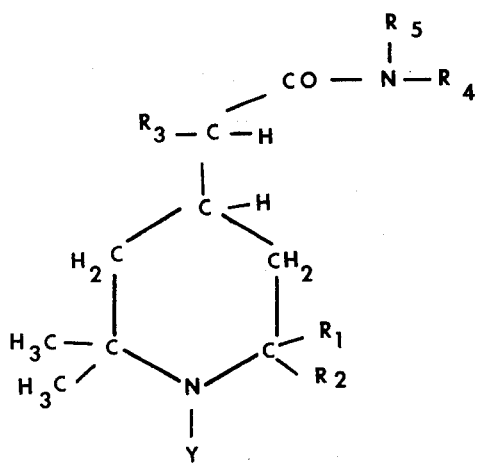

wherein
Y is straight- or branched alkyl having from 1 to 12 carbon atoms, alkenyl having from 3 to 12 carbon atoms, benzyl, α-methyl-benzyl, p-methyl benzyl, α, p-dimethylbenzyl, α-napthylmethyl, 2-phenyl-2-hydroxyethyl or a group $R_7$-CH OH-CH$_2$- wherein $R_7$ is hydrogen, alkyl having from 12 to 4 carbon atoms or phenyl.

$R_1$ and $R_2$ are the same or different and each is straight- or branched alkyl having from 1 to 12 carbon atoms or $R_1$ and $R_2$, together with the carbon atom to which they are attached, form a cycloalkyl group having from 5 to 12 carbon atoms.

$R_3$ and $R_5$ are independently hydrogen, straight-or branched alkyl having from 1 to 4 carbon atoms, benzyl, α-methyl benzyl, α, p- dimethylbenzyl or a cycloalkyl group having 5 or 6 carbon atoms.

$R_4$ is hydrogen, a hydrocarbyl group having from 1 to 20 carbon atoms and being either unsubstituted or substituted by halogen or interrupted by one or more oxygen or sulphur atoms or a salt of the amine function of a compound of formula I said salt being selected from the phosphate, carbonate, sulphate, chloride, acetate, stearate, malonate, citrate, tartrate or oxalate salt.

2. A compound according to claim 1 wherein $R_4$ is an alkyl group having from 1 to 20 carbon atoms, an alicyclic group having from 5 to 20 carbon atoms, benzyl, α-methyl benzyl, α,p-di- methyl benzyl, diphenylmethyl, 2-chlorobenzyl, 2- or 9-fluorenyl, 1- adamantyl, phenyl, 4- methyl phenyl, 4-t-octylphenyl, 2-chloro-phenyl, 4-methoxyphenyl, α-naphthyl or 4-biphenyl.

3. A compound according to claim 1 wherein Y is methyl.

4. A compound according to claim 3 wherein $R_1$ and $R_2$ are each methyl.

5. A compound according to claim 4 wherein $R_3$ and $R_5$ are each hydrogen.

6. A compound according to claim 1 which is N-dodecyl-(1,2,2,6,6-pentamethyl-piperidinyl-4)-acetamide.

7. The compound of claim 1 which is N-n-butyl(1,2,2,6,6-pentamethylpiperidinyl-4) acetamide.

8. The compound of claim 1 which is N-(n-hexyl)(1,2,2,6,6-pentamethylpiperidinyl-4)acetamide.

9. The compound of claim 1 which is N-(n-octyl)(1,2,2,6,6-pentamethylpiperidinyl-4) acetamide.

10. The compound of claim 1 which is N-(n-octadecyl)(1,2,2,6,6-pentamethylpiperidinyl-4) acetamide.

11. The compound of claim 1 which is N-cyclohexyl(1,2,2,6,6-pentamethylpiperidinyl-4) acetamide.

12. The compound of claim 1 which is N-cyclohexyl(1-ethyl-2,2,6,6-tetramethylpiperidinyl-4)acetamide.

13. The compound of claim 1 which is N-benzyl(1,2,2,6,6-pentamethylpiperidinyl-4) acetamide.

14. The compound of claim 1 which is N-phenyl(1,2,2,6,6-pentamethylpiperidinyl-4) acetamide.

15. The compound of claim 1 which is N-(4'-chlorobutyl)(1,2,2,6,6-pentamethylpiperidinyl-4)acetamide.

16. (N-(2'-methoxyphenyl)(1,2,2,6,6-pentamethylpiperidinyl-4) acetamide.

17. α-(n-butyl)-N-cyclohexyl (1,2,2,6,6-pentamethyl-piperidinyl-4) acetamide.

18. N-allyl (1,2,2,6,6-pentamethylpiperidinyl-4) acetamide.

* * * * *